United States Patent
Asgharian

(10) Patent No.: US 8,563,011 B2
(45) Date of Patent: *Oct. 22, 2013

(54) USE OF LOW MOLECULAR WEIGHT AMINO ALCOHOLS IN OPHTHALMIC COMPOSITIONS

(75) Inventor: Bahram Asgharian, Arlington, TX (US)

(73) Assignee: Alcon Research, Ltd., Fort Worth, TX (US)

(*) Notice: Subject to any disclaimer, the term of this patent is extended or adjusted under 35 U.S.C. 154(b) by 608 days.

This patent is subject to a terminal disclaimer.

(21) Appl. No.: 11/343,068

(22) Filed: Jan. 30, 2006

(65) Prior Publication Data
US 2006/0264516 A1    Nov. 23, 2006

Related U.S. Application Data

(63) Continuation of application No. 11/168,788, filed on Jun. 28, 2005, now Pat. No. 7,045,095, which is a continuation of application No. 10/007,423, filed on Oct. 22, 2001, now Pat. No. 6,949,218, which is a continuation of application No. 09/308,456, filed as application No. PCT/US97/20826 on Nov. 17, 1997, now Pat. No. 6,319,464.

(60) Provisional application No. 60/033,079, filed on Dec. 13, 1996.

(51) Int. Cl.
A61K 9/00 (2006.01)
A61K 31/04 (2006.01)

(52) U.S. Cl.
USPC .......................................... 424/400; 514/740

(58) Field of Classification Search
USPC .......................................... 424/400; 514/740
See application file for complete search history.

(56) References Cited

U.S. PATENT DOCUMENTS

| | | | |
|---|---|---|---|
| 3,966,905 A * | 6/1976 | Nite | 514/653 |
| 4,407,791 A | 10/1983 | Stark | |
| 4,469,684 A * | 9/1984 | Huggins et al. | 514/29 |
| 4,525,346 A | 6/1985 | Stark | |
| 4,620,979 A * | 11/1986 | Schachar | 424/678 |
| 4,732,185 A | 3/1988 | Cowle et al. | |
| 4,734,475 A | 3/1988 | Goldenberg et al. | |
| 4,758,595 A | 7/1988 | Ogunbiyi et al. | |
| 4,766,151 A | 8/1988 | Leclerc et al. | |
| 4,829,083 A | 5/1989 | Doulakas | |
| 4,829,088 A | 5/1989 | Doulakas | |
| 4,904,359 A | 2/1990 | Pancheri et al. | |
| 4,975,466 A | 12/1990 | Bottcher et al. | |
| 5,034,230 A * | 7/1991 | Morita et al. | 424/427 |
| 5,096,607 A * | 3/1992 | Mowrey-McKee et al. | 422/28 |
| 5,171,526 A | 12/1992 | Wong et al. | |
| 5,260,021 A | 11/1993 | Zeleznick | |
| 5,281,277 A | 1/1994 | Nakagawa et al. | |
| 5,290,774 A * | 3/1994 | Morita et al. | 514/218 |
| 5,342,620 A | 8/1994 | Chowhan | |
| 5,356,555 A | 10/1994 | Huth et al. | |
| 5,393,491 A | 2/1995 | Dassanayake et al. | |
| 5,422,073 A | 6/1995 | Mowrey-McKee et al. | |
| 5,451,237 A | 9/1995 | Vehige | |
| 5,460,658 A | 10/1995 | Nakagawa et al. | |
| 5,505,953 A | 4/1996 | Chowhan | |
| 5,531,917 A | 7/1996 | Nakayama et al. | |
| 5,540,864 A * | 7/1996 | Michael | 510/181 |
| 5,573,726 A | 11/1996 | Dassanayake et al. | |
| 5,603,929 A | 2/1997 | Desai et al. | |
| 5,631,005 A | 5/1997 | Dassanayake et al. | |
| 5,958,387 A | 9/1999 | Bara et al. | |
| 6,319,464 B1 * | 11/2001 | Asgharian | 422/28 |
| 6,949,218 B2 * | 9/2005 | Asgharian | 422/28 |

FOREIGN PATENT DOCUMENTS

| | | |
|---|---|---|
| CA | 2098472 | 12/1993 |
| EP | 0 888 780 A1 | 1/1999 |
| JP | 5-58967 | 3/1993 |
| JP | 8-194192 | 7/1996 |
| JP | 9-30966 | 2/1997 |
| WO | 91/17469 | 11/1991 |
| WO | WO 92/11876 | 7/1992 |
| WO | WO 9321903 A1 * | 11/1993 |
| WO | WO 94/19027 | 9/1994 |
| WO | 95/09905 | 4/1995 |
| WO | 95/26756 | 10/1995 |
| WO | 96/00275 | 1/1996 |
| WO | WO 96/02624 | 2/1996 |
| WO | WO 96/03158 A1 | 2/1996 |
| WO | WO 96/03973 | 2/1996 |
| WO | WO 9607724 A1 * | 3/1996 |
| WO | WO 98/20912 | 5/1998 |

OTHER PUBLICATIONS

Merck Index Results, Epinephrine, Sep. 20, 2007, http:themerckindex.cambridgesoft.com/TheMerckIndex/default.asp?formproup=basenp_form_group&dataaction=db&dbname=TheMerckIndex, 2 pages.*
Merck Index Results, Phenylephrine, Sep. 20, 2007, http:themerckindex.cambridgesoft.com/TheMerckIndex/default.asp?formproup=basenp_form_group&dataaction=db&dbname=TheMerckIndex, 1 page.*
Anonymous, Pharmaceutical solution containing sodium cromoglycate, Research Disclosure Journal, Oct. 1990, RD318050, printed from http://www.rdjournal.co.uk/rd/search/RD318050.pdf on Aug. 27, 2010, 4 pages.*
Wang et al., Solubility of N2O in alkanolamines and in mixed solvents, The Chemical Engineering Journal, vol. 48, Issue 1, Jan. 1992, printed from http://www.sciencedirect.com/, Abstract only, 2 pages.*
Document bibliography and abstract of Japanese Patent No. 5-58967, esp@cenet database.
Document bibliography and abstract of Japanese Patent No. 8-194192, esp@cenet database.

(Continued)

Primary Examiner — Gigi Huang
(74) Attorney, Agent, or Firm — Mark E. Flanigan

(57) ABSTRACT

The use of low molecular weight amino alcohols in ophthalmic compositions is described. These compounds have been found to enhance the efficacy of anti-microbial preservatives.

10 Claims, No Drawings

(56) References Cited

OTHER PUBLICATIONS

Document bibliography and abstract of Japanese Patent No. 9-30966, esp@cenet database.

Merck Index 12$^{th}$ Editions "Tromethamine Monograph", p. 1664, (1996).

Angus Chemical Company Technical Bulletin TB 69, "Tris Amino® Tris(Hydroxymethyl)Aminomethane", p. 1-4, (1999).

Document bibliography and abstract of Japanese Patent No. 5-58967, esp@cenet database, Mar. 9, 1993.

Document bibliography and abstract of Japanese Patent No. 8-194192, esp@cenet database, Jul. 30, 1996.

Document bibliography and abstract of Japanese Patent No. 9-30966, esp@cenet database, Feb. 4, 1997.

Angus Chemical Company Marketing Benchmarks AMB 51, "Tris Amino® (Tris Buffer) Applications in Eye-Care Pharmaceuticals", p. 1-4, (2000).

Harper, et al.; "Simple Additives to Increase the Activity of Chlorhexidine Digluconate Against Urinary Pathogens", *Paraplegia*, vol. 21, pp. 86-93, (1983).

Wooley, et al., "Action of Edta-Tris and Antimicrobial Agent Combinations on Selected Pathogenic Bacteria", *Veterinary Microbiology*, vol. 8, pp. 271-280, (1983).

* cited by examiner

USE OF LOW MOLECULAR WEIGHT AMINO ALCOHOLS IN OPHTHALMIC COMPOSITIONS

The present application is a continuation of U.S. patent application Ser. No. 11/168,788 filed Jun. 28, 2005 now U.S. Pat. No. 7,045,095 (now allowed), which is a continuation of U.S. patent application Ser. No. 10/007,423 filed Oct. 22, 2001 (now U.S. Pat. No. 6,949,218), which is a continuation of U.S. patent application Ser. No. 09/308,456 filed May 14, 1999 (now U.S. Pat. No. 6,319,464), which claims benefits to PCT/US97/20826 filed Nov. 17, 1997, and Provisional Application No. 60/033,079 filed Dec. 13, 1996.

BACKGROUND OF THE INVENTION

The present invention relates to the field of ophthalmology. More specifically, the invention relates to the use of low molecular weight amino alcohols in products for treating contact lenses, as well as other ophthalmic products. The amino alcohols described herein have been found to be useful in preserving ophthalmic compositions. The amino alcohols have also been found to be useful in enhancing the activity of anti-microbial preservatives, and have been found to be particularly effective when combined with borate or borate/polyol buffer systems.

Ophthalmic compositions generally must include an anti-microbial agent to prevent contamination of the compositions by bacteria, fungi and other microbes. Such compositions may come into contact with the cornea either directly or indirectly. The cornea is particularly sensitive to exogenous chemical agents. Consequently, in order to minimize the potential for harmful effects on the cornea, it is necessary to use anti-microbial agents which are relatively non-toxic to the cornea, and to use such agents at the lowest possible concentrations (i.e., the minimum amounts required in order to perform their anti-microbial functions). This balancing of the anti-microbial efficacy and potential toxicological activity of anti-microbial agents is sometimes difficult to achieve. More specifically, the anti-microbial agent concentration necessary for useful preservation of ophthalmic formation or disinfection of contact lenses may create the potential for toxicological effects on the cornea and/or other ophthalmic tissues. Using lower concentrations of the anti-microbial agents generally helps to reduce the potential for such toxicological effects, but the lower concentrations may be less effective for biocidal efficacy of ophthalmic compositions. This weaker activity may create the potential for microbial contamination of the compositions and ophthalmic infections resulting from such contaminations. This is also a serious problem, since ophthalmic infections involving *pseudomonas aeruginosa* or other virulent microorganisms can lead to loss of visual function or even loss of the eye. Thus, there is a need for a means of enhancing the activity of anti-microbial agents so that very low concentrations of these agents can be utilized without increasing the potential for toxicological effects or increasing the risk of microbial contamination and resulting ophthalmic infections.

Numerous anti-microbial agents have been used or suggested in the art for preserving ophthalmic compositions or disinfecting contact lenses. Such agents have included: benzalkonium chloride (BAC), thimerosal, chlorhexidine, polymeric biguanides, such as polyhexylmethyl biguanides (PHMB), and polymeric quaternary ammonium agents, such as polyquaternium-1. Other agents have included alkylamines, such as the amidoamines described in U.S. Pat. No. 5,393,491 (Dassanayake et al.) and U.S. Pat. No. 5,573,776 (Dassanayake et al.). While all of these agents have offered some level of utility, their use has also led to certain limitations or drawbacks. For example, thimerosal, which contains mercury, has caused severe ocular irritation resulting from contact lens disinfecting; BAC tends to complex in a detrimental way with negative ionic species typical in ophthalmic compositions and the polymeric biguanides and quaternary ammonium agents, although less ophthalmically irritating/toxic, have limited anti-microbial efficacy against certain species of fungi, including *Aspergillus fumigatus* and *Aspergillus niger*. Furthermore, new FDA disinfecting requirements are now being implemented which require even a greater magnitude of microbial kill against a greater number of microorganisms. Thus, a need exists for enhancing the effectiveness of these otherwise useful anti-microbial agents.

Compositions for treating contact lenses and other types of ophthalmic compositions are generally formulated as isotonic, buffered solutions. One approach to enhancing the anti-microbial activity of such compositions is to include multi-functional components in the compositions. In addition to performing their primary functions, such as cleaning or wetting contact lens surfaces (e.g., surfactants), buffering the compositions (e.g., borate), or chelating undesirable ions (e.g., EDTA), these multi-functional components also serve to enhance the overall anti-microbial activity of the compositions. For example, ethylenediaminetetraacetic acid and the monosodium, disodium and trisodium salts thereof (collectively referred to herein as "EDTA") has been widely used for many years in ophthalmic products, particularly products for treating contact lenses. It has been used in such products for various purposes, but particularly for its supplemental anti-microbial activity and as a chelating agent. The inclusion of EDTA in contact lens care products and other ophthalmic compositions enhances the anti-microbial efficacy of chemical preservatives contained in such compositions, particularly the efficacy of those preservatives against gram negative bacteria.

Borate buffer systems are used in various types of ophthalmic compositions. For example, two commercial solutions for disinfecting contact lenses, OPTI-SOFT® (0.001% polyquaternium-1) Disinfecting Solution marketed by Alcon Laboratories, Inc. and ReNu® Multi-Purpose Solution (0.00005% polyhexamethylene biguanide) marketed by Bausch & Lomb, Inc., contain borate buffer systems which contribute to the disinfecting efficacy of the solutions. An improved borate buffer system for ophthalmic compositions is described in U.S. Pat. No. 5,342,620 (Chowhan) and U.S. Pat. No. 5,505,953 (Chowhan). That system utilizes borate in combination with one or more polyols, such as mannitol. This combination enhances the anti-microbial activity of compositions, beyond the enhancement obtained with borate alone. However, the present inventors have found that the water soluble complex formed by the borate/polyol also reduces the pH of compositions significantly. As a result of efforts directed to solving this and other problems, the present inventors have discovered that certain amino alcohols can be effectively and safely utilized to provide pH-buffering of ophthalmic compositions and to further enhance the anti-microbial activity of the compositions.

The use of tromethamine in compositions and methods for disinfecting contact lenses is described in U.S. Pat. No. 5,422,073 (Mowrey-McKee, et al.). This publication indicates that a synergistic effect is obtained when tromethamine is combined with other known microbicides and chelating agents. EDTA is identified as the preferred chelating agent.

In view of the foregoing, there is a need for an improved means for enhancing the activity of anti-microbial agents so as to preserve ophthalmic compositions from microbial contamination and disinfect contact lenses more efficaciously. The present invention is directed to satisfying this need.

SUMMARY OF THE INVENTION

The present invention is based on a new use of a specific group of low molecular weight amino alcohols. The present inventors have found that the amino alcohols described herein enhance the activity of anti-microbial agents, particularly when utilized in combination with borate or borate/polyol buffer systems. The enhancement is more than additive. Thus, although the mechanisms of action are not fully understood, it is believed that the low molecular weight amino alcohols of the present invention produce a synergistic enhancement of anti-microbial activity.

The present inventors have also found that the subject amino alcohols are very effective in neutralizing the acid pH of borate/polyol complexes. This buffering effect of the amino alcohols is significant. Although conventional bases, such as sodium hydroxide, may be utilized to adjust the pH of acidic solutions containing borate/polyol complexes, the amino alcohols described herein have a significantly higher buffering capacity. This enhanced buffering capacity is particularly important if the compositions contain anti-microbial agents which are pH dependent (e.g., alkyl amidoamines). If the pH of such compositions is not maintained within the range required for maximum anti-microbial activity, the overall anti-microbial activity of the composition may be reduced. The use of borate-polyol buffering system may also significantly reduce the amount of NaOH necessary for pH adjustments, and therefore reduce the amount of ions in the compositions. This feature is particularly significant when ion sensitive anti-microbial agents, such as polyquaternium-1, are employed.

The amino alcohols may be used in various types of ophthalmic compositions, particularly compositions for treating contact lenses, such as disinfectants, cleaners, comfort drops and rewetting drops. The low molecular weight amino alcohols are particularly useful in compositions for disinfecting, rinsing, storing and/or cleaning contact lenses. When these compounds are combined with borate buffer systems, the combination also helps to preserve the products against microbial contamination. This anti-microbial effect of the amino alcohol/borate combination reduces the amount of anti-microbial agent required for preservative purposes, and in some instances, may totally eliminate the need for a conventional anti-microbial preservative agent.

The present invention is particularly directed to the provision of improved compositions for disinfecting contact lenses. The compositions have significantly enhanced anti-microbial activity, relative to prior compositions containing the same primary disinfecting agents (e.g., polyquaternium-1). The enhancement is achieved by means of a combination of formulation criteria, including the use of a borate/polyol complex and one or more amino alcohols, as described herein. This enhancement of anti-microbial activity is highly significant. Preferred disinfecting compositions also contain a relatively small amount of an alkylamine. New government regulations in some countries have, in effect, created a need for compositions having significantly greater anti-microbial activity. More specifically, the new regulations require that compositions for disinfecting contact lenses be capable of achieving disinfection without assistance from other compositions (e.g., cleaning compositions or preserved saline rinsing solutions). The enhancement of anti-microbial activity achieved by means of the present invention enables contact lens disinfecting compositions to satisfy this standard.

DETAILED DESCRIPTION OF THE INVENTION

The low molecular weight amino alcohols which may be utilized in the present invention are water soluble and have a molecular weight in the range of from about 60 to about 200. The following compounds are representative of the low molecular weight amino alcohols which may be utilized in the present invention: 2-amino-2-methyl-1-propanol (AMP), 2-dimethylamino-methyl-1-propanol (DMAMP), 2-amino-2-ethyl-1,3-propanediol (AEPD), 2-amino-2-methyl-1,3-propanediol (AMPD), 2-amino-1-butanol (AB). "AMP (95%)", which refers to 95% pure AMP and 5% water, is the most preferred low molecular weight amino alcohol of the present invention. These amino alcohols are available commercially from Angus Chemical Company (Buffalo Grove, Ill.).

The amount of amino alcohol used will depend on the molecular weight of the amino alcohol selected, the other ingredients in the composition, i.e., other anti-microbial agents, chelating agents, buffering agents, tonicity agents, and the function of the anti-microbial agents contained in the ophthalmic compositions (i.e., preservation of compositions or disinfection of contact lenses). In general, one or more of the above-described amino alcohols will be utilized in a concentration of from about 0.01 to about 2.0 percent by weight/volume ("% w/v"), and preferably from 0.1 to 1.0% w/v. When borate/polyol complexes are employed with the amino alcohol compositions of the present invention, the amino alcohols will generally be present in an amount necessary to neutralize the pH of the complex, or bring the composition to a desired pH. This amount, therefore, is a function of the particular borate/polyol mixture and concentration.

The low molecular weight amino alcohols described herein may be included in various types of ophthalmic compositions to enhance anti-microbial activity, or for the other purposes mentioned above. Examples of such compositions include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of compositions, such as ocular lubricating products, artificial tears, astringents, and so on. The compositions may be aqueous or non-aqueous, but will generally be aqueous.

In addition to the low molecular weight amino alcohols described above, the compositions of the present invention may contain one or more anti-microbial agents to preserve the compositions from microbial contamination and/or disinfect contact lenses. For example, the compositions may contain the anti-microbial agent known as polyquaternium-1 or POLYQUAD® (registered trademark of Alcon Laboratories, Inc.); the use of this agent as a preservative in ophthalmic compositions is described in U.S. Pat. No. 4,525,346 (Stark). The entire contents of the Stark '346 patent are hereby incorporated in the present specification by reference. Additional examples of anti-microbial agents include chlorhexidine, alexidine, hexetidine, polyhexamethylene biguanide, benzalkonium chloride, benzododecinum bromide, alkylamines, alkyl di-, tri-amine and other anti-microbial agents utilized as anti-microbial preservatives or disinfecting agents in ophthalmic compositions. The inclusion of one or more of the above-described low molecular weight amino alcohols in ophthalmic compositions containing such anti-microbial agents enhances the overall anti-microbial activity of the compositions. This enhancement is particularly evident when the compositions include a borate or borate-polyol buffer system.

As indicated above, the low molecular weight amino alcohols described above are preferably used in combination with borate or borate/polyol buffer systems. As used herein, the term borate shall refer to boric acid, salts of boric acid and other pharmaceutically acceptable borates, or combinations thereof. The following borates are particularly preferred: boric acid, sodium borate, potassium borate, calcium borate, magnesium borate, manganese borate, and other such borate salts. As used herein, and unless otherwise indicated, the term polyol shall refer to any compound having at least two adjacent —OH groups which are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol and sorbitol. Especially preferred polyols are mannitol and sorbitol; most preferred is sorbitol. The use of borate-polyol complexes in ophthalmic compositions is described in commonly assigned U.S. Pat. No. 5,342,620 (Chowhan) and U.S. Pat. No. 5,505,953 (Chowhan); the entire contents of which are hereby incorporated in the present specification by reference. The '953 patent identifies propylene glycol as a preferred polyol for use in the borate/poly complexes described therein. The compositions of the present invention preferably contain one or more borates in an amount of from about 0.01 to about 2.0% w/v, more preferably from about 0.3 to 1.2% w/v, and one or more polyols in an amount of from about 0.01 to 5.0% w/v, more preferably from about 0.6 to 2.0% w/v.

As stated above, current disinfecting compositions are unable to meet the new FDA requirements for disinfecting efficacy of contact lens disinfecting compositions. The compositions of the present invention improve on these prior art compositions with the inclusion of amino alcohols in the compositions. The most preferred contact lens disinfecting compositions of the present invention comprise one or more low molecular weight amino alcohol(s), a borate-polyol buffer, an anti-microbial agent, as described above, and an alkylamine.

Alkylamines have been described in commonly owned U.S. Pat. No. 5,393,491 (Dassanayake et al.), U.S. Pat. No. 5,573,726 (Dassanayake et al.), and U.S. Pat. No. 5,631,005 (Dassanayake, et al.). The foregoing patents are hereby incorporated in the present specification by reference. These alkylamines possess both anti-bacterial and anti-fungal activity. Preferred alkylamines are the amidoamines, as described in the above-referenced Dassanayake et al. patents. The most preferred amidoamine is myristamidopropyldimethyl-amine ("MAPDA").

The amount of alkylamine in the compositions of the present invention will vary, due to various factors such as: anti-microbial potency and potential toxicity of the particular alkylamine. The present inventors have found, however, that the amount of alkylamines, particularly the amidoamines, useful in the compositions of the present invention is dramatically lower when combined with compositions comprising borate buffers, than when the alkylamines are employed without borates. Generally, the alkylamines will be present in concentrations of from about 0.00005 to about 0.01% w/v, when combined with borates.

As will be appreciated by those skilled in the art, the preserving or disinfecting compositions may also contain a wide variety of other ingredients, such as tonicity agents (e.g., sodium chloride or mannitol), surfactants (e.g., alkyl ethoxylates and polyoxyethylene/polyoxypropylene copolymers), and viscosity adjusting agents. The present invention is not limited with respect to the types of ophthalmic compositions in which the other low molecular weight amino alcohols described above are utilized.

All of the above-described compositions will be formulated so as to be compatible with the eye and/or contact lenses to be treated with the compositions. As will be appreciated by those skilled in the art, the ophthalmic compositions intended for direct application to the eye will be formulated so as to have a pH and tonicity which are compatible with the eye. This will normally require a buffer to maintain the pH of the composition at or near physiologic pH (i.e., 7.4) and may require a tonicity agent to bring the osmolality of the composition to a level at or near 210-320 milliosmoles per kilogram (mOsm/kg). The formulation of compositions for disinfecting and/or cleaning contact lenses will involve similar considerations, as well as considerations relating to the physical effect of the compositions on contact lens materials and the potential for binding or absorption of the components of the composition by the lens.

The following examples are presented to further illustrate selected embodiments of the present invention.

Example 1

The following saline solutions containing various amino alcohols at a concentration of 1.2% were prepared for comparative purposes. The composition of the solutions is presented below. The pH of the solutions was adjusted to 7.4 with hydrochloric acid. The amino alcohols consisted of 2-amino-2-methyl-1-propanol (AMP), 2-dimethylamino-methyl-1-propanol (DMAMP), 2-amino-2-ethyl-1,3-propanediol (AEPD), 2-amino-2-methyl-1,3-propanediol (AMPD), and 1,4-Bis(2-hydroxyethyl)-piperazine (BHP). The osmolalities of the solutions were 335, 250, 254, 304 and 208 mOsm/kg, respectively.

| Ingredients | Amount (w/v %) |
| --- | --- |
| Amino Alcohol | 1.2% |
| Sodium Chloride | 0.3% |
| Disodium Edetate | 0.05% |
| Purified Water | QS |

The antibacterial activity of the above-described saline solutions against $S.$ $marcescens$ was evaluated. The formulations were evaluated by inoculating 20 ml of each solution with 0.1 ml of a microbial suspension. The final concentration was $10^6$ colony forming units ("CFUs") per ml. At each time point, pour plates of SCDA were prepared containing diluted aliquots of the various test samples. The bacteria and yeast plates were incubated at 30° to 35° C. for 2 to 3 days. The mold plates were incubated at 20° to 25° C. for five days. Following the colony incubation period, the number of CFUs were counted and the log reduction of the CFUs relative to the starting amount was calculated. The results at 6 and 24 hours (in log reduction of survivors) are shown in Table 1 below:

TABLE 1

| Amino Alcohol | Log Reduction of Survivors | |
|---|---|---|
| | 6 hours | 24 hours |
| AMP | 0.1 | 0.5 |
| DMAMP | 0.0 | 0.7 |
| AEPD | 0.0 | 0.7 |
| AMPD | 0.0 | 0.0 |
| BHP | 0.1 | 0.1 |

As indicated by the foregoing data, all of the formulations exhibited minimal activity against *S. marcescens*.

Example 2

The following is an example of a preserving composition of the present invention (Formulation A) and a comparative composition (Formulation B). Both formulations, contain a borate/polyol buffer system (i.e., boric acid and mannitol), but differ in that Formulation A utilizes AMP (95%) and Formulation B utilizes NaOH to adjust the pH. The formulations were prepared by first sequentially dissolving in 90 ml of purified water, boric acid, mannitol, poloxamine and disodium edetate. AMP (95%) was added to Formulation A and the volume was adjusted to 100 ml with purified water. The pH of Formulation A was 7.4. The pH of Formulation B was adjusted to 7.4 with 6N NaOH, and the volume of the solution was adjusted to 100 ml with purified water. Both formulations had an osmolality of about 200 mOsm/kg. The compositions of the two formulations are set forth below:

| | Amount (w/v %) | |
|---|---|---|
| Ingredients | Formulation A | Formulation B |
| Boric Acid | 1.0% | 1.0% |
| Mannitol | 1.5% | 1.5% |
| Disodium Edetate | 0.05% | 0.05% |
| Polaxamine | 0.1% | 0.1% |
| AMP (95%) | 0.56% | — |
| Sodium hydroxide | — | pH to 7.4 |
| Purified Water | QS | QS |

The anti-microbial activity of the formulations against *S. marcescens* and *P. aeruginosa* was evaluated. A similar microbial protocol to the Example 1 protocol was employed The results are presented in Table 2 below:

TABLE 2

| Microorganism | Time | Formulation A | Formulation B |
|---|---|---|---|
| *S. marcescens* | 6 hours | 0.1 | 0.0 |
| | 24 hours | 1.1 | 0.2 |
| | 168 hours | 4.5 | 1.5 |
| *P. aeruginosa* | 6 hours | 5.0 | 1.0 |
| | 24 hours | 6.0 | 1.4 |

Note:
Underline numbers represent no survivors.

As indicated by the foregoing data, Formulation A exhibited significantly greater antibacterial activity than Formulation B, which does not contain an amino alcohol in accordance with the present invention. This example demonstrates that the effect of amino alcohol in a borate composition surpasses the anti-bacterial effect of EDTA alone (Formulation B).

Example 3

The following is a comparative example of a preserving and/or disinfecting composition of the present invention (Formulation C) and a comparative composition (Formulation D). Two formulations similar to those described in Example 2 above, but containing the anti-microbial agent POLYQUAD®, were prepared. The formulations were prepared by means of procedures similar to those described in Example 2, above. POLYQUAD® was added before final pH adjustment. The pH of formulation C was 7.4; the pH of Formulation D was adjusted to pH 7.4 with 6N NaOH. The composition of the formulations is presented below:

| | Amount (w/v %) | |
|---|---|---|
| Ingredients | Formulation C | Formulation D |
| Boric Acid | 1.0% | 1.0% |
| Mannitol | 1.5% | 1.5% |
| Disodium Edetate | 0.05% | 0.05% |
| Polaxamine | 0.1% | 0.1% |
| POLYQUAD® | 0.0005% | 0.0005% |
| AMP (95%) | 0.56% | — |
| Sodium Hydroxide | — | pH to 7.4 |
| Purified Water | QS | QS |

The anti-microbial activity of the formulations against *S. marcescens*, *S. aureus* and *P. aeruginosa* was evaluated. Microbial protocols similar to the Example 1 protocol were employed. The results are presented in Table 3 below:

TABLE 3

| Microorganism | Time | Formulation C | Formulation D |
|---|---|---|---|
| *S. marcescens* | 6 hours | 2.9 | 2.4 |
| | 24 hours | 3.3 | 3.0 |
| | 168 hours | 6.1 | 4.8 |
| *S. aureus* | 6 hours | 5.1 | 4.4 |
| | 24 hours | 6.1 | 5.9 |
| *P. aeruginosa* | 6 hours | 6.0 | 5.3 |
| | 24 hours | 6.0 | 6.0 |

Note:
the underline numbers represent no survivors.

These results demonstrate that the amino alcohol contained in Formulation C significantly enhanced the anti-microbial activity of the composition.

Example 4

The following is a preferred multi-purpose composition for the cleaning, disinfecting, rinsing and storing of soft hydrophilic lenses:

| Ingredient | % (w/v) |
|---|---|
| Polyquaternium-1 | 0.001 |
| Boric acid | 0.6 |
| Sorbitol | 1.2 |
| Sodium chloride | 0.1 |
| Sodium citrate | 0.65 |
| Tetronic 1304 | 0.05 |
| Disodium Edetate | 0.05 |
| Sodium hydroxide | pH 7.8 |
| Hydrochloric acid | pH 7.8 |
| Purified water | QS |
| AMP (95%) | 0.45% |
| MAPDA | 0.0005% |

The anti-microbial activity of the above composition against *A. fumigatus, C. albicans, F. solani, P. aeruginosa, S.*

*marcescens*, *S. aureus* and *S. warneri* was evaluated. Microbial protocols similar to that of Example 1 for the various microorganisms were employed. The results are illustrated in Table 4, below:

TABLE 4

| Microorganism | Time (Hrs) | Log Reduction |
|---|---|---|
| *A. fumigatus* ATCC 10894 | 4 | 2.2 |
| | 6 | 3.1 |
| | 24 | 4.8 |
| | 48 | 4.8 |
| *C. albicans* ATCC 10231 | 4 | 1.5 |
| | 6 | 1.7 |
| | 24 | 2.7 |
| | 48 | 4.0 |
| *F. solani* ATCC 36031 | 4 | 3.8 |
| | 6 | 4.3 |
| | 24 | 5.6 |
| | 48 | 5.8 |
| *P. aeruginosa* ATCC 9027 | 4 | 4.7 |
| | 6 | 5.7 |
| | 24 | 6.1 |
| | 48 | 6.1 |
| *S. marcescens* ATCC 13880 | 4 | 3.3 |
| | 6 | 4.1 |
| | 24 | 6.0 |
| | 48 | 4.7 |
| *S. marcescens* ATCC 14041 | 4 | 2.1 |
| | 6 | 2.7 |
| | 24 | 5.6 |
| | 48 | 5.6 |
| *S. aureus* ATCC 6538 | 4 | 3.7 |
| | 6 | 3.7 |
| | 24 | 5.5 |
| | 48 | 6.1 |
| *S. warneri* ATCC 17917 | 4 | 4.9 |
| | 6 | 5.1 |
| | 24 | 5.9 |
| | 48 | 5.9 |

Example 5

The following is a comparative example of a multi-purpose composition of the present invention (Formulation E) and a comparative composition (Formulation F). The two formulations are the same, except that Formulation F does not contain EDTA.

| Component | Formulation E | Formulation F |
|---|---|---|
| | Concentration (% w/v) | |
| MAPDA | 0.0005 | 0.0005 |
| AMP (95%) | 0.45 | 0.45 |
| Boric Acid | 0.6 | 0.6 |
| Polyquaternium-1 | 0.001 | 0.001 |
| Sodium Citrate | 0.65 | 0.65 |
| Sodium Chloride | 0.1 | 0.1 |
| Sorbitol | 1.2 | 1.2 |
| Tetronic 1304 | 0.05 | 0.05 |
| Disodium EDTA | 0.05 | — |
| NaOH/HCl | pH 7.8 | pH 7.8 |
| Purified Water | QS | QS |

The anti-microbial activity of the above compositions against *P. aeruginosa*, *S. marcescens*, *S. aureus*, and *C. albicans* was evaluated using a protocol similar to that of Example 1, above. The log reduction data is illustrated in Table 5, below:

TABLE 5

| Microorganism | Time (Hrs) | Formulation E | Formulation F |
|---|---|---|---|
| *P. aeruginosa* | 6 | 4.7 | 4.7 |
| ATCC 9027 | 24 | <u>6.0</u> | <u>6.0</u> |
| *S. marcescens* | 6 | 3.2 | 3.3 |
| ATCC 13880 | 24 | 5.1 | 4.9 |
| *S. aureus* | 6 | 3.9 | 3.6 |
| ATCC 6538 | 24 | 4.9 | <u>6.1</u> |
| *C. albicans* | 6 | 1.1 | 1.4 |
| ATCC 10231 | 24 | 4.3 | 5.1 |

Note:
Underlined number indicates no survivors

Example 6

The following composition is an example of a multi-purpose composition useful for cleaning, rinsing, disinfecting and conditioning Rigid Gas Permeable (RGP) lenses:

| Component | Amount |
|---|---|
| Hydroxy propyl methyl cellulose | 0.4% |
| Tetronic 1304 | 0.5% |
| Boric Acid | 0.6% |
| Sorbitol | 1.2% |
| Disodium Edetate | 0.01% |
| AMP (95%) | 0.4% |
| Propylene glycol | 0.5% |
| Polyquaternium-1 | 0.0005% |
| NaOH/HCl | pH 7.6 |
| Purified water | QS |

The anti-microbial activity of the above composition against against *S. marcescens*, *S. aureus*, and *C. albicans* was evaluated using a protocol similar to that of Example 1, above. The log reduction data is illustrated in Table 6, below:

TABLE 6

| Microorganism | Time | $Log_{10}$ Reduction of Survivors |
|---|---|---|
| *C. albicans* | 4 | 3.6 |
| | 6 | 4.1 |
| | 24 | 5.3 |
| *S. marcescens* | 4 | 3.6 |
| | 6 | 2.6 |
| | 24 | 5.5 |
| *S. aureus* | 4 | 5.1 |
| | 6 | 4.8 |
| | 24 | <u>6.1</u> |

Note:
Underlined number indicates no survivors

Example 7

The following is an example of a disinfecting composition useful for soft hydrophilic lenses.

| Component | Amount |
|---|---|
| Boric Acid | 0.1% |
| Sorbitol | 0.2% |
| AMP (95%) | 0.07% |
| Propylene glycol | 1.4% |
| DS EDTA | 0.01% |

-continued

| Component | Amount |
|---|---|
| Polyquaternium-1 | 0.0001% |
| NaOH/HCl | pH 7.6 |
| Purified water | QS |

The anti-microbial activity of the above composition against against *S. marcescens, S. aureus*, and *C. albicans* was evaluated using a protocol similar to that of Example 1, above. The log reduction data is illustrated in Table 7, below:

TABLE 7

| Microorganism | Time | Log$_{10}$ Reduction of Survivors |
|---|---|---|
| *C. albicans* | 6 | 1.5 |
| | 24 | 3.0 |
| *S. marcescens* | 6 | 4.6 |
| | 24 | <u>6.2</u> |
| *S. aureus* | 6 | 2.7 |
| | 24 | 5.1 |

Note:
Underlined number indicates no survivors

What is claimed is:

1. A sterile ophthalmic composition for treating contact lenses wherein the ophthalmic composition is free of any pharmaceutical agent for the treatment of glaucoma, infection, inflammation or allergy; and comprises 0.1 to 2.0 w/v % of a low molecular weight amino alcohol with a molecular weight of from 60 to 200 and a borate/polyol buffer; wherein the composition is a contact lens cleaning and disinfecting solution that exhibits significantly enhanced anti-microbial activity against *S. marcescens* and *P. aeruginosa* due to the inclusion of the amino alcohol and the amino alcohol is selected from the group consisting of 2-amino-2-methyl-1-propanol (AMP), 2-dimethylamino-methyl-1-propanol (DMAMP), 2-amino-2-ethyl-1,3-propanediol (AEPD), 2-amino-2-methyl-1,3-propanediol (AMPD), 2-amino-1-butanol (AB), and combinations thereof; and the ophthalmic composition has a pH and tonicity which are compatible with the eye.

2. A composition as in claim 1 wherein the amino alcohol is AMP.

3. A composition as in claim 1 wherein the solution has an osmolality at 210-320 milliosmoles per kilogram such that it is compatible with an eye.

4. A composition as in claim 1 wherein the solution has a pH at 7.4.

5. A composition as in claim 1 wherein the solution further comprises a polymeric quaternary ammonium agent.

6. A composition as in claim 5 wherein the polymeric quaternary ammonium agent is polyquaternium-1.

7. A composition as in claim 5 wherein the polymeric quaternary ammonium agent is a polymeric biguanide.

8. A composition as in claim 7 wherein the polymeric biguanide is polyhexylmethyl biguanide.

9. A composition as in claim 1 wherein the pH of the composition is from 7.4 to 7.8.

10. A composition as in claim 1 wherein the polyol is selected from the group consisting of mannitol and sorbitol.

* * * * *